US005550239A

United States Patent [19]

Humora et al.

[11] Patent Number: 5,550,239

[45] Date of Patent: Aug. 27, 1996

[54] PROCESS FOR LARGE-SCALE PRODUCTION OF INDOLYL ALKYL PYRIMIDINYL PIPERAZINE COMPOUNDS

[75] Inventors: Michael J. Humora, Cranbury; Sandeep P. Modi, Monmouth Junction; Sushi K. Srivastava, Dayton, all of N.J.; Andrew D. Williams, Middletown, Conn.

[73] Assignee: Bristol-Myers Squibb Company, New York, N.Y.

[21] Appl. No.: 336,022

[22] Filed: Nov. 8, 1994

[51] Int. Cl.[6] .................................................. C07D 403/14

[52] U.S. Cl. ............................................................ 544/295

[58] Field of Search ............................................... 544/295

[56] References Cited

U.S. PATENT DOCUMENTS 5,300,506 4/1994 Smith et al. ............................ 514/253

OTHER PUBLICATIONS

Larock et al, "Synthesis of Indoles via Palladium–Catalyzed Heteroannulation of Internal Alkynes," *Journal of American Chemical Society*, 1991, 113, pp. 6689–6690.

*Primary Examiner*—Mukund J. Shah
*Assistant Examiner*—Matthew V. Grumbling
*Attorney, Agent, or Firm*—Richard P. Ryan

[57] ABSTRACT

An improved, novel convergent process suitable for large scale preparation of the antimigraine agent 4-(5-methoxy-4-pyrimidinyl)-1-[3-[5-[[(methylamino)sulfonyl]methyl]-1H-indol-3-yl]propyl]piperazine (BMS 180048) and close analogs. The improved process provides efficiencies in handling, purification, and product yield and involves a novel heteroannulation reaction that provides the indole ring moiety and propylpiperazinyl-pyrimidine backbone in a single step.

13 Claims, No Drawings

PROCESS FOR LARGE-SCALE PRODUCTION OF INDOLYL ALKYL PYRIMIDINYL PIPERAZINE COMPOUNDS

BACKGROUND OF THE INVENTION

This invention comprises an improved, more economical process for the synthesis of BMS 180048 and analogs. Importantly, the process can be adapted to large-scale manufacture. BMS 180048 is chemically 4-(5-methoxy-4-pyrimidinyl)-1-[3-[5-[[(methylamino)sulfonyl]methyl]-1 H-indol-3-yl]propyl]piperazine. Synthesis of BMS 180048 and related compounds has been disclosed by Smith, et al. in U.S. Pat. No. 5,300,506, issued Apr. 5, 1994. BMS 180048 and its analogs are antimigraine agents. Currently, BMS 180048 itself is undergoing clinical trials to establish the safety and efficacy of its use in treating vascular headache in patients.

The demand for drug substance has increased substantially with the advent of clinical testing, and a future need for much larger amounts of BMS 180048 is projected due to its intended commercialization. The prior art processes for preparation of BMS 180048 and its analogs proved to be unsatisfactory for adaption to the larger scale production required to meet these demands for large quantities of the drug. The prior art process utilized for synthesis of BMS 180048 and close analogs is set out in Scheme A.

In Scheme A, R can be hydrogen, lower alkyl or trifluoromethyl and $R^1$ can be hydrogen, lower alkyl or phenyl-lower alkyl. $R^2$ and $R^3$ are independently selected from hydrogen and methyl and $R^4$ is lower alkyl. The symbol n denotes zero or the integers 1 and 2. For BMS 180048: R is methyl; $R^1$, $R^2$, and $R^3$ are hydrogen; $R^4$ is methyl and n is 1. The compound Y-X denotes reagents that convert hydroxy groups into leaving groups and could be e.g. HBr, Cl—$SO_2$Me, etc. Other designations are standard in organic synthesis and are defined infra.

This prior art process is that disclosed by Smith, et. al. with methods of synthesis for the starting materials also being disclosed, e.g. see Example 5 of U.S. Pat. No. 5,300,506 for preparation of the iodoaniline intermediate (IV). As can be appreciated from examination of Scheme A, the final step comprises the coupling reaction of the indolylalkyl component (XV) with the pyrimidinylpiperazine component (VI). Intermediate (XV) is by far the more precious component. Syntheses of pyrimidinylpiperazines are straightforward (e.g. see Examples 21–24 of U.S. Pat. No. 5,300,506) and are amenable to scale-up. On the other hand, construction of compound (XV) requires several steps from intermediate (IV). A process problem with the coupling of (XV) and (VI) is that if the nucleofuge (leaving group, X), that is selected is very labile, e.g. iodide, a second molecule of (XV) attaches to the pyrimidine ring at the 1-nitrogen position to give a quaternary pyrimidinium salt impurity which occurs in yields on the order of10% or more. Selection of a less labile nucleofuge, e.g. mesylate, results in less efficient coupling with a concomitant reduction in overall process yield.

It is further appreciated by those skilled in process development that many processes, procedures, and/or reactions are not amenable to being carried out on a large scale as is done in a pilot plant or a manufacturing facility. Some examples of situations where scale-up can be problematic may involve the use of hazardous or toxic reagents and/or solvents; highly exothermic reactions; high pressure or high vacuum processes, such as those required for certain high pressure reactions or high vacuum distillations; chromatographic separation and/or purification. Also troublesome are processes exhibiting reduced yield on scale-up and the like. A more recent consideration for large scale operations is the limitations which have been set on certain emissions as well as the disposal of waste products from chemical processing. Processes involving these aspects incur higher levels of cost in production.

The prior art process for preparation of BMS 180048 is not amenable to scale-up for many of the reasons listed above as well as other process problems unique to the actual reactions employed. For example: key intermediates in the prior art process such as (XVI) and (XV) are not crystalline materials, thereby complicating purification and handling procedures; product isolated after deprotection is of low quality and end product is contaminated by residual palladium. The most serious drawback, however, was the actual cost of product produced by adaption of the prior art process for large-scale preparation of BMS 180048. A major objective of the present invention then is to provide a synthetic process whose cost considerations allow its utilization on a large scale to be economical.

SUMMARY OF DETAILED DESCRIPTION OF THE INVENTION

This invention relates to an improved synthetic process which is adaptable for large-scale production of 4-(5-methoxy-4-pyrimidinyl)-1-[3-[5-[[(methylamino)sulfonyl]methyl]-1H-indol-3-yl]propyl]piperazine (BMS 180048), a compound possessing useful antimigraine properties. This improved process offers advantages in economies of chemical intermediates, reagents, product purification, time and labor costs. In addition, the improved process can be successfully scaled-up in size to more economically provide larger amounts of the required product.

As a first consideration, the improved process is a convergent synthesis, as opposed to a lengthy prior art linear synthesis. Rather than constructing the product molecule in a linear stepwise fashion, the left and right halves of the molecule are constructed separately and then joined in a crucial step of the improved process. In a chemical process, each step in the sequence leading from the starting material can be viewed as a "value-added" operation, thereby increasing the cost and value of each new intermediate along the path, i.e. each intermediate becomes more valuable than its precursor compound. In the prior art process, the attachment of the pyrimidinylpiperazine component to the indolylalkyl component only yielded about 60% of coupled product with about 40% of the precious indolylalkyl intermediate (XV) being lost. In the convergent synthetic process of the present invention, process efficiency is obtained in terms of increased yield of intermediates as fewer steps are required to reach any intermediate in the process.

The improved process of this invention allowing efficient scale-up is outlined in Scheme B. In Scheme B, R is hydrogen, lower alkyl and trifluoromethyl and $R^1$ is hydrogen, lower alkyl and phenyl-lower alkyl. $R^2$ and $R^3$ are independently selected from hydrogen and methyl; $R^4$ and $R^5$ are independently selected from lower alkyl. The symbol n denotes zero or the integers 1 and 2. For synthesis of BMS 180048, R is methyl; $R^1$, $R^2$ and $R^3$ are hydrogen; $R^4$ is methyl and n is 1.

The process of Scheme B essentially comprises the coupling of a trialkylsilyl derivative of a pentynylpiperazine compound of Formula (V) with an alkoxy-halo-pyrimidine derivative of Formula (VII) (generated from compound (IX) in situ) to provide compound (III). The designation "LG" in compound (VIII) refers to an organic leaving group with a preferred example being methanesulfonyl (mesyl) which is easily obtained by treating a 4-pentyn-1-ol derivative with methanesulfonyl chloride for example.

Compound (III) is then condensed with the iodoaniline intermediate of Formula (IV), utilizing a palladium-catalyzed heteroannulation reaction to provide a 2-$(R^5)_3$-Si-indole compound (II). In this improved process, a less expensive, less toxic lithium salt is used in place of tetra-n-butylammonium salt of the prior art. Similarly, the solvent, previously DMF, is replaced by alcohol making a significant improvement for a large-scale process. Treatment of (II) with mineral acid, preferably HCl, provides the Formula (I) product. Modification of the workup by recrystallization of the HCI salt from hot water results in higher purity of the base product free of contaminating palladium.

Some additional advantages of the improved instant process of Scheme B are that the key intermediates in the process are crystalline and the heteroannulation reaction forming the indole nucleus proceeds with at least a 10% higher yield without regio-isomer contamination compared to the old process. A primary advantage of the improved process is its convergent nature. Rather than building the product molecule (I) in the stepwise fashion of a linear synthesis, the left and right halves of the molecule are constructed separately and then joined. This is much more efficient in terms of chemical yield, since not as many steps are required to reach any given intermediate. One of the lower yielding steps in the prior art process is the attachment of the pyrimidinylpiperazine to the hydroxypropylindole. If a 60% yield was obtained, this meant that 40% of the precious indolic half of the compound was lost. This coupling now occurs between the trialkylsilyl derivative of pentynylpiperazine (V) and the relatively trivial pyrimidinyl intermediate (VII). The pyrimidine (VII) can be synthesized in high-yielding reactions that are technically simple. By utilizing the pentynylpiperazine (V) intermediate in the instant process instead of a pyrimidinylpiperazine of the prior art process, the much cheaper reagent piperazine can be utilized instead of the more expensive more-N-protected piperazine as a starting material. This reaction sequence also improves on the previous process as a troublesome bis-byproduct is eliminated by delaying introduction of the pyrimidine moiety until this step.

An uncertain aspect beforehand regarding this improved synthesis was whether the palladium catalyzed heteroannulation would occur in the presence of a piperazine ring. The piperazine could serve as a ligand for the palladium catalyst, competing with the aniline, thus deactivating it through a steric or electronic mechanism. Success or failure of the heteroannulation under these circumstances was certainly not predictable beforehand. This is evidenced by comparing prior art reports of such heteroannulations (cf: LaRock, J.A.C.S. 1991, 113, 6689–6690), where not only are there no piperazine-containing substrates, there are no amines of any type other than the required aniline moieties.

The success then of the improved instant synthesis was largely dependent on achievement of the heteroannulation process to produce the indole moiety in the presence of the strongly basic and nucleophilic piperazine ring. Unexpected efficiency of the new process resulted from higher yields of the heteroannulated product although the new improved process involved reactants containing a potentially interfering piperazine ring compared to the prior art process where the reactants lacked any amine moiety that could compete with the intended aniline annulation. The efficiency of the new improved process was further enhanced by incorporation of easily purifiable crystalline intermediates to replace compounds in the form of oils in the prior art processes.

Other inefficiencies of the prior art process have been overcome in the new improved process. Both old and new processes utilize the iodoaniline intermediate (IV). A compound (IV) intermediate appropriate for BMS 180048 synthesis can be obtained as shown in Scheme C.

In the prior process, as shown in Scheme A, the 4-amino-3-iodo-N-methylbenzene-sulfonamide (IV) was reacted with a suitable protected alkynol compound (XVIII) and heteroannulated at that point to arrive at the hydroxypropylindolesulfonamide compound (XVI). This valuable intermediate then was activated and coupled with the pyrimidinylpiperazine component (VI) to provide the final product in only about 60% yield from (XVI). The new process, in contrast, is a direct convergent synthesis with the indole nucleus and other framework of the product molecule being established at the end of the sequence and overall in higher yield utilizing much less expensive intermediates, e.g., compounds (V) and (III) as opposed to compounds (XVI) and (XV).

The improved process for synthesis of BMS 180048 itself proceeds by coupling (IV) with a trialkylsilyl-N-pentynylpiperazinylpyrimidine intermediate (III), which is obtained as shown in Scheme D.

For use in the improved process, intermediates wherein $R^5$ is ethyl or propyl are preferred with ethyl being most preferred. The $R^5$=ethyl compounds are useful novel intermediates having the advantage in that they yield a heteroannulation product essentially free of the other undesired regioisomer wherein the propylpiperazinylpyrimidinyl side-chain is attached at the indole-2-position and the trialkylsilyl group is bonded to the indole-3-position.

Heteroannulation proceeds immediately by heating the coupled product of (IV) and (III) in the presence of palladium acetate; triphenylphosphine, a lithium halide, e.g., lithium chloride; and sodium carbonate in alcohol, ethanol being preferred. Treatment of this reaction product (II) with mineral acid, HCl being preferred, removes the trialkylsilyl group from the indole 2-position and provides BMS 180048 (I). This deprotection reaction was previously accomplished with HF in acetonitrile-conditions that would be undesirable in large-scale processing.

In sum, the new improved process provides BMS 180048 and close analogs in a more efficient convergent synthetic process that eliminates problems caused by troublesome impurities and/or lowered yields, as well as substituting crystalline intermediates, having improved ease of handling, separation and purification compared with intermediate compound oils of the prior synthetic process.

The improved process meets the stated objectives of providing a practical synthetic process that can be utilized economically on the large scale required for production of BMS 180048. The process is essentially a four step process compatible with large scale chemical processing equipment. Process modifications have been discovered and incorporated which:

- eliminate the formation of a troublesome quaternary pyrimidinium salt impurity without sacrificing higher yield;
- eliminate vacuum distillation and chromatographic purification requirements for reaction intermediates;
- simplify separation and purification of reaction intermediates; and provide the final product in improved yield and purity at a lower cost.

DESCRIPTION OF SPECIFIC EMBODIMENTS

The improved process of this invention is illustrated in greater detail by the following examples directed to preferred embodiments of the hereinabove described process steps. These examples, however, should not be construed as limiting the scope of the present invention in any way.

A. Preparation of Starting Materials

EXAMPLE 1

4-Amino-3-iodo-N-methylbenzenemethane sulfonamide (IV)

1) Sodium 4-nitrobenzyl sulfonate

Materials:

| | |
|---|---|
| 4-Nitrobenzylbromide | 1000 (4.63 moles) |
| Sodium sulfite | 642 g (5.09 moles) |
| Methanol | 3955 mL |
| $H_2O$ | 5000 mL |

Procedure:

Into a 22 L 3-necked flask equipped with an overhead stirrer, condenser, nitrogen inlet, temperature probe, and heating mantle were charged the benzyl bromide, sodium sulfite, methanol and water. The reaction slurry was heated to reflux under nitrogen and then stirred at reflux temperature for two hours. After this period of time, the solution was orange in color. Heating was discontinued and then the reaction allowed to slowly cool to ambient temperature overnight. The reaction may be monitored by TLC (Silica gel; Dichloromethane; $R_f$ s.m.=0.95; $R_f$ product=0.0.

The reaction slurry was chilled to 0° C. and then stirred at this temperature for 2.5 hours to obtain a thick slurry. The product was collected by filtration and then washed on the filter with 4 L of cold (0° C.) isopropyl alcohol. The isolated, cream-colored product was then dried in vacuo at 55° C. for ~48 hours to constant weight to yield 912 g (82.4%) of desired sulfonate salt which was used "as is" in the next reaction.

2) 4-Nitro-N-methylbenzenemethanesulfonamide

Materials:

| | |
|---|---|
| Sodium sulfonate salt (from 1) | 555 (2.32 moles) |
| $PCl_5$ | 580 (2.79 moles) |
| 40% aq. Methylamine | 400 mL (5.15 moles) |
| Toluene | 7000 ml |

Procedure:

The sodium salt (555.0 grams) was charged into a 12-liter three-necked flask equipped with a Dean Stark trap. Seven liters of toluene was added. The mixture was then heated to reflux. The toluene/water azeotrope was collected (1000 ml). A total of 55 mL of water was obtained. Heating was discontinued and the mixture was allowed to cool to room temperature. To this mixture was then added 580 grams of $PCl_5$ portionwise over 15 minutes. No exotherm was observed during this addition. The mixture was slowly (2.5 hours) heated to reflux. The mixture was then heated at reflux temperature for two hours. Acidic gas evolution ceases after ~1.5 hours of refluxing time. The yellow tan hazy solution was allowed to cool to room temperature. A total of 12 liters of methylene chloride was then added to the reaction mixture. The organic solution was washed with 4 liters of water followed by 4 liters of a 1:1 brine/saturated sodium bicarbonate solution. The rich organic layer was then dried over anhydrous magnesium sulfate. The solution was filtered and then the magnesium sulfate cake was washed with additional methylene chloride.

A total of 400 mL of 40% aqueous methyl amine was added to the organic solution over 0.5 hours. The reaction exotherm caused a temperature rise from 19° C. to 34° C. The reaction was held overnight at ambient temperature. The solution was then concentrated in vacuo to remove methylene chloride. The resulting slurry was chilled to 0° C. and then filtered. The cake was washed with water (2×500 mL) and dried at 50° C. in vacuo to constant weight to yield 374.5 g (79%) of the nitrobenzene sulfonamide intermediate.

3) 4-Amino-N-methylbenzenemethanesulfonamide

Materials:

| | |
|---|---|
| "nitro solfonamide" (from 2) | 439 (1.91 moles) |
| 5% Pd/C* | 140 g |
| 2N HCl | 993 mL |
| $H_2O$ | 4360 mL |
| EtOH | 2180 mL |

*Degussa "water wet" SP1-871

Procedure:

The "nitro sulfonamide" (439 g) was suspended in a solution of $H_2O$ (4360 mL) and EtOH (2180 mL) in a 12-liter, 3-necked, round-bottomed flask equipped with an overhead stirrer and a gas dispersion tube. 993 mL of 2N HCl was added and nitrogen gas was sparged through the solution for 5–10 minutes. 5% Pd/C (140 g) was added to the mixture under nitrogen and the mixture was purged with nitrogen again for 5 minutes. The mixture was warmed to 35°–40° C. in a warm water bath and sparged with hydrogen gas at that temperature for 10 to 16 hours until the reaction is complete. The progress of the reaction was monitored by TLC: Silica gel; EtOAc: Hexane 7:3; "nitro sulfonamide" $R_f$=0.73, "amino sulfonamide" $R_f$=0.53; UV detection. When the reaction was deemed complete by TLC analysis, it was sparged with nitrogen for 10–15 minutes before filtering through a Celite pad. Concentrated the reaction mixture in vacuo to remove the bulk of the ethanol and basified the aqueous reaction mixture with 50% NaOH solution from pH 2.9 to pH 10.5. The product started to precipitate from the aqueous solution during the course of the basification. Chilled the mixture to 0°–5° C. and held at that temperature for one hour. Filtered the resultant solid and washed the solid thoroughly with cold (5° C.) water (2×1 L). Dried the solid in vacuo at 45° C. for ~48 hours to a constant weight to yield ~340 g of desired product (88%). This material was used without further purification in the next step of the reaction sequence.

4) 4-Amino-3-iodo-N-methylbenzenemethanesulfonamide

Materials:

| | |
|---|---|
| 4-amino-N-methyl-benzene-methanesulfonamide (from 3) | 290 g |
| Sodium bicarbonate | 243.6 g |
| Sodium bicarbonate | 2.25 L |
| Iodine | 736.6 g |

Procedure:

The sodium bicarbonate, water and amino sulfonamide were agitated at room temperature in a 12 L 3-neck round bottom flask and under a nitrogen atmosphere. Added 1 equivalent of iodine to the reaction mix and the color changed from a pale yellow slurry to a brown/red slurry.

After one hour reaction time added the second equivalent of iodine to flask. Reaction monitored by HPLC for completion and in general, the reaction goes to 90% completion.

The dark brown reaction mix was diluted with 4.35 L of ethyl acetate and 1.45 L of saturated sodium thiosulphate solution. The organic layer was separated and washed with 2×1.5 L of saturated sodium thiosulfate and 3 L of ethyl acetate. The water layer was extracted with 3 L of ethyl acetate. The combined organic layers were washed with 2 L of saturated sodium thiosulfate and dried over 300 g of magnesium sulfate and 50 g of activated charcoal (Darco G-60). The dark wine-colored solution was concentrated to a slurry and 15 L of saturated sodium thiosulfate solution was added to the slurry followed by agitation for 1 hour. The slurry was filtered and washed with water (1 L). The brown dense material was oven-dried overnight to give an 85% weight yield of the compound (IV) intermediate.

EXAMPLE 2

1-(5-trimethylsilyl-1-pent-4-ynyl)piperazine (V)

1) 1-Hydroxy-5-trimethylsilylpent-4-yne
Materials:

| | | |
|---|---|---|
| 4-Pentyn-1-ol | 20.0 g | (0.238 mole) |
| Ethylmagnesium bromide | 500 mL | of 1M THF solution (0.5 mole) |
| Trimethylsilyl chloride | 55.2 g | (0.508 mole) |

Procedure:

The 4-pentyn-1-ol and 400 mL of anhydrous THF were stirred in a 2 L, 3-necked flask under a nitrogen atmosphere. The ethyl-magnesium bromide solution was added while keeping the reaction temperature in a range of 25° to 35° C. After stirring the resultant solution for 4–5 hours at ambient temperature, the trimethylsilyl chloride was added to the reaction while keeping the reaction at 0°–10° C. under the nitrogen atmosphere. After completion of the addition, the reaction was stirred at ambient temperature for an additional 1–2 hours to allow for completion of reaction.

The reaction mixture was cooled to 0°–5° C. and acidified by the addition of 100 to 120 mL 1N HCl (pH becomes less than 2). After stirring at 0–10° C. for an additional 1–2 hours, the reaction mixture was extracted with EtOAc (about 400 mL) and the EtOAc layer was separated, washed with 190–210 mL of 5% $NaHCO_3$ solution and then with deionized water (about 200 mL). The EtOAc solution was concentrated to an approximate volume of 400 mL and this EtOAc solution of the TMS-pentynol was used in the next step.

2) 1-Methanesulfonyl-5-trimethylsilylpent-4-yne
Materials:

| | |
|---|---|
| TMS-pentynol (from 1) | about 400 mL EtOAc solution |
| Triethylamine | 30.4 g (0.30 mole) |
| Methanesulfonayl chloride | 30.0 g (0.26 mole) |

Procedure:

To a stirred mixture of the triethylamine and the EtOAc solution containing the TMS-pentynol was added the mesyl chloride via an addition funnel. The stirred reaction mixture was maintained at 0°–10° C. under an inert atmosphere during the mesyl chloride addition and for a period of 1–2 hours thereafter.

The reaction was quenched by addition of 2.5% $NaHCO_3$ solution (about 140 mL) to the stirred reaction solution. The organic phase was separated and water washed (about 140 mL deionized water) and then filtered. The filtrate was concentrated to about 400 mL by distillation of the EtOAc and this EtOAc solution of the mesyl intermediate was used without further purification in the next step. Concentration of the intermediate was determined by GC for a known volume of the EtOAc solution.

3) 1-(5-trimethylsilyl-1-pent-4-ynyl)piperazine (V)
Materials:

| | | |
|---|---|---|
| TMS-pentynylmesylate (from 2) | 25 g | (about 250 mL of EtOAc solution; 0.1 mole) |
| piperazine | 92.2 g | (10 mole) |

Procedure:

Under a nitrogen atmosphere the EtOAc solvent was removed by distillation and replaced with acetonitrile. This solution was added over a period of 10–45 minutes to a hot solution of piperazine in acetonitrile maintained at 70° to 80° C. The resulting suspension was stirred at reflux (about 90°–93° C.) and then cooled to about 45° C. t-Butyl methyl ether (400 mL) was added to the reaction mixture followed by deionized water (200 mL) while maintaining the temperature at 35°–40° C.

The organic layer was separated and washed two times with 200 mL portions of water to remove the excess piperazine. The organic layer was then extracted with 1.5N HOAc (250 mL) followed by two 70 mL washes with 1.5N HOAc. The acetic acid solutions were combined and the pH adjusted to >9.0 with a 25% solution of sodium carbonate in deionized water. An organic phase formed a top layer on this basified reaction mixture and the organic phase was separated. The aqueous phase was extracted with t-butyl methyl ether (300 mL) and the extract combined with the initial organic phase. The combined organic portions were washed with a saturated NaCl solution to provide a t-butyl methyl ether solution comprised of about 93% by weight of the ether and 7% of compound (V). This 7% solution remains stable at ambient temperature for up to 18 days if protected from light.

EXAMPLE 3

1-(5-triethylsilyl-1-pent-4-ynyl)piperazine (V)

1) 1-Hydroxy-5-triethylsilylpent-4-yne
Materials:

| | |
|---|---|
| 4-Pentynyl-1-ol | 20 (0.2377 moles) |
| Ethylmagnesium Chloride (2M in THF) | 258 mL (0.500 moles) |
| Triethylsilyl chloride | 39.5 g (0.262 moles) |

Procedure:

The 4-pentyn-1-ol and 100 mL of anhydrous tetrahydrofuran were placed in a 1 L, 3-necked flask under a nitrogen atmosphere. The resulting solution was cooled to 0° to 5° C. with stirring. The ethylmagnesium chloride solution was added while maintaining the batch temperature between 0° to 40° C. After stirring the resultant solution for 5–6 hours at 37° to 42° C., a solution of triethylsilyl chloride in 50 mL of anhydrous THF was added via an addition funnel while the temperature was kept between 30° to 42° C. After completion of the addition, the reaction was cooled to ambient temperature and stirred for 2–3 hours for completion of reaction.

The reaction mixture was cooled to 0° to 5° C. and acidified with 240 to 260 mL 1N HCl (solution apparent pH becomes less than 2). The reaction mixture was stirred at 15° to 25° C. for an additional 3–5 hours to complete the reaction and the aqueous phase was separated. To the product rich organic phase 50 mL (5 w/v %) aqueous sodium bicarbonate solution was added and the aqueous phase was separated (pH of aqueous should be greater than 7.5). The product rich organic phase was concentrated under reduced pressure and THF was replaced with EtOAc. The distillation was terminated when the solution KF reached 0.2% or less and a batch volume of 300 to 400 mL was achieved. This solution was used directly in the next step.

2) 1-Methanesulfonyl-5-triethylsilylpent-4-yne

Materials:

| | |
|---|---|
| TES-Pentynol (from 1) | ~300 to 400 mL EtOAc solution |
| Triethylamine | 25.4 g (0.251 moles) |
| Methanesulfonyl chloride | 25.6 g (0.223 moles) |

Procedure:

To a stirred, cooled mixture of triethylamine and the ethyl acetate solution containing the TES-pentynol was added the mesyl chloride. The reaction mixture was stirred at 0° to 10° C. under nitrogen atmosphere for 1–2 hours to complete the reaction. Completion of the reaction can be monitored by GC with the reaction being complete when the relative area of the TES-Pentynol is less than half that of the mesylated product.

The reaction was quenched by addition of 2.5% $NaHCO_3$ solution (about 130 mL) with stirring while the batch temperature was maintained between 0° to 10° C. The organic phase was separated and washed with water (~130 mL). After polish filtration, the separated organic phase was concentrated to a 400 mL solution showing KF≦0.1. This EtOAc solution of the mesyl intermediate was used in the next step without further purification. Concentration of the intermediate was determined by GC and by gravometric analysis for a known volume of the EtOAc solution.

3) 1-(5-triethylsilylpent-4-ynyl)piperazine

Materials:

| | | |
|---|---|---|
| TES-Pentynylmesylate (from 2) | 54 g | (400 mL EtOAc, solution, (0.196 moles) |
| piperazine | 174 g | (2.02 moles) |

Procedure:

Under a nitrogen atmosphere the EtOAc solvent was removed by distillation and replaced with acetonitrile. This solution was added over a period of 10 to 45 minutes to a hot solution of piperazine in 195 mL of acetonitrile maintained at 70° to 80° C. The reaction mixture was stirred at this temperature until reaction was judged complete by GC analysis (about 5 to 10 minutes) and then cooled to 45° C. t-Butyl methyl ether (1200 mL) was added, followed by deionized water (450 mL), while the temperature of the mixture was maintained at 35° to 45° C.

The organic phase was separated and washed twice with 450 mL portions of water at 30° to 40° C. to remove the excess piperazine. The organic layer was then extracted with 1.5N AcOH (~240 mL) followed by two additional ~240 mL washes with 1.5N AcOH. The acetic acid solutions were combined and the pH was adjusted to >9.0 with a 33% solution of sodium carbonate in deionized water. The resulting mixture was extracted with t-butyl methyl ether (650 mL) and the organic layer was then washed with saturated NaCl solution to provide a t-butyl ether solution comprise of about 7% by weight of product (V) and 93% of t-butyl methyl ether. This 7% solution is used in the next step and remains stable at ambient temperature for up to 15 days if protected from light.

EXAMPLE 4

4-Chloro-5-methoxypyrimidine (VII)

Materials:

| | |
|---|---|
| 4-hydroxy-5-methoxypyrimidine | 11.2 g (0.089 moles) |
| Phosphorous Oxychloride ($POCl_3$) | 9.1 mL (0.098 moles) |
| N-diisopropylethylamine (DIPEA) | 17.1 mL (0.098 moles) |

Procedure:

To a stirred slurry of 4-hydroxy-5-methoxypyrimidine in toluene (171 mL) was added DIPEA and $POCl_3$ at room temperature under nitrogen atmosphere, The reaction mixture was stirred for about 1–2 hours at 60° to 70° C. under nitrogen atmosphere to complete the reaction.

The reaction was quenched by adding 90 mL of 1.55N NaOH at 5° to 8° C. and the aqueous phase was separated. The organic layer was washed with saturated $NaHCO_3$ solution (31 mL) and polish filtered. Concentration of the intermediate was determined by HPLC quantitation. This 0.37 to 0.43M solution of chloromethoxypyrimidine was used without further purification,

EXAMPLE 5

1-(5-Methoxy-4-pyrimidinyl)-1-(4-piperazinyl)-5-trimethylsilyl-4-pentyne

Materials:

| | | |
|---|---|---|
| 1-(5-trimethylsilyl-1-pent-4-ynyl)piperazine (V) (63 mg/mL solution from example 2.3) | 15.12 g | (~240 mL of MTBE solution; 0.067 moles) |
| 4-Chloro-5-methoxypyrimidine (0.37 molar solution from example 4) | 10.71 g | (~202 mL of Toluene solution; 0.074 moles) |
| Triethylamine | 10.3 mL | (0.074 moles) |

Procedure:

Under nitrogen atmosphere, the t-butyl methyl ether solution of (V) was concentrated to a volume of 23 mL, and then the toluene solution containing chloromethoxypyrimidine and triethylamine was added. The resulting solution was heated to reflux with stirring until reaction was judged complete by GC (about 3–4 hours). The reaction mixture was cooled to room temperature and washed successively with 210 mL deionized water and 210 mL 5% $NaHCO_3$ solution.

The organic layer was then extracted with two 135 mL portions of 1N HCl and the product rich aqueous fractions were combined. The combined aqueous phase was extracted with 200 mL toluene to remove organic soluble impurities. After removing the residual toluene from the aqueous phase by vacuum distillation, the solution was cooled to 15° to 20° C. and pH of the solution was adjusted to 4.2 by addition of 2N NaOH solution from a dropping funnel. At this stage seed crystals (~30 mg) were added and the addition of the 2N NaOH solution was continued until a cloud point was reached (pH 4.7 to 5.1). Addition of the NaOH solution was stopped and the resulting slurry was stirred for about 1 hour. Additional 2N NaOH solution was added to the slurry until pH=8±0.2 was reached. The crystal slurry was stirred for 0.5 hour at 15°–20° C. while the mixture was maintained at pH ~8. Product was isolated by filtration, washed with cold deionized water (0° to 5° C.) and dried under vacuum at 35° to 40° C. The intermediate was obtained in 89M % yield (20.7 g) having 99+ area % by GC and HPLC.

EXAMPLE 6

1-(5-Methoxy-4-pyrimidinyl)-1-(4-piperazinyl)-5-triethylsilyl-4-pentyne

Materials:

| | | |
|---|---|---|
| 1-(5-triethylsilylpent-4-ynyl)piperazine (V) example 3.3) | 40 g | (~632 mL of MTBE solution; 0.15 moles) |
| 4-Chloro-5-methoxypyrimidine (0.37 molar solution from example 4) | 23.87 g | (~398 mL of Toluene solution; 0.165 moles) |
| Triethylamine | 23 mL | (16.7 g; 0.165 moles) |
| Phosphoric acid (85% solution in water) | 18.2 g | (0.158 moles) |

Procedure:

Under nitrogen atmosphere, t-butyl methyl ether solution of (V) was concentrated to a volume of 106 mL, and then toluene solution containing chloromethoxypyrimidine and triethylamine was added. The resulting solution was heated to reflux with stirring until reaction was judged complete by GC (about 3–4 hours). The reaction mixture was cooled to room temperature and washed successively with 400 mL deionized water and 400 mL 5% $NaHCO_3$ solution.

The organic layer was concentrated to a volume of about 180 mL under reduced pressure and 295 mL of acetonitrile was then added. The solution was heated to 35°–40° C. and a phosphoric acid solution in 100 mL acetonitrile was added over about 2 hours. The resulting slurry was cooled to 20°–25° C. and stirred for one half hour and then heated to 30°–35° C. and stirred for one half hour. Finally slurry was cooled to 0°–5° C., and after stirring for one and half hour, product was isolated by filtration and washed with 250 mL acetonitrile. The product was dried at 40°–50° C. to afford 66.7 g of product (III) in 94.1M % yield (HPLC 99.7 area %).

B. Preparation of Product

EXAMPLE 7

Coupling of 4-amino-3-iodo-N-methylbenzenemethanesulfonamide (IV) with 1-(5-methoxy-4-pyrimidinyl)-1-(4-piperazinyl)-5-trimethylsilyl-4-pentyne (III: $R^5$=Me)

Materials:

| | |
|---|---|
| Compound (IV) | 21.9 kg |
| Compound (III) | 24.1 kg |
| Sodium carbonate | 35.3 kg |
| Sodium carbonate | 35.3 kg |
| Triphenylphosphine | 2.63 kg |
| Lithium chloride | 3.07 kg |
| Palladium acetate | 0.75 kg |
| 190 proof ethanol | 171.3 kg |
| Hy-Flo ® (diatomaceous earth filter aid) | 2.25 kg |

-continued

| | |
|---|---|
| Trithiocyanuric acid | 2.20 kg |
| THF | 102.4 kg |

Procedure:

Into a 250 gallon reactor equipped with an overhead stirrer, condenser, nitrogen inlet, temperature probe and a heating jacket were charged the sodium carbonate, triphenylphosphine, lithium chloride, palladium acetate, compound (IV) and compound (III), and 190 proof ethanol. The reaction slurry was heated to reflux under nitrogen and then stirred at reflux temperature for 17 hours. After this period of time, the slurry was dark brown in color. Heating was discontinued and the slurry was allowed to cool to ambient temperature. Hy-Flo®, trithiocyanuric acid and THF (48.6 kg) were charged into the reactor. The resulting slurry was heated to reflux under nitrogen and then stirred at reflux temperature for 1 hour. Heating was discontinued and the slurry was chilled to 0° C. and then stirred at this temperature for 1 hour. The inorganic salts were removed by filtration and then washed with 53.7 kg of cold (0° C.) THF. The filtrate and wash were used "as is" in the deprotection reaction.

EXAMPLE 8

Preparation of 3-[3-[4-(5-Methoxy-4-pyrimidinyl)-1-piperazinyl] propyl]-N-methyl-H-indole-5-methanesulfonamide (I; BMS 180048)

Materials:

| TMS-indole derivative (III) (from Example 7) | |
|---|---|
| Water | 44.2 kg |
| THF | 48.6 kg |
| Conc. HCl | 41.8 kg |
| 190 proof ethanol | 111.4 kg |

Procedure:

The solution of compound (II) in ethanol-THF (from Example 7), THF and water was charged to another 200 gallon reactor. The reaction solution was cooled to 0° C. and then treated with conc. HCl. The reaction slurry was stirred at ambient temperature for 2 hours. After this period of time, the reaction may be monitored by HPLC.

The reaction slurry was chilled to 0° C. and then stirred at this temperature for 2 hours to obtain a thick slurry. The product was collected by filtration and then washed with cold ethanol to provide a light beige colored solid. This material was loaded into a 100 gallon reactor equipped with overhead stirrer, condenser, thermocouple, and heating jacket along with water (204.2 kg) and decolorizing charcoal (Darco®; 2.0 kg). The reaction mixture was heated to 70° to 75° C. and stirred at that temperature for 1 hour. After this period of time, the reaction mixture was cooled to 65° C. and filtered to remove Darco®. The Darco cake was washed with 28 L of hot (60° C.) water. The resulting filtrate and wash were combined and allowed to slowly cool to ambient temperature overnight.

The reaction filtrate was chilled to 0° C. and then stirred at this temperature for 2 hours to obtain a thick slurry. The HCl salt product was collected by filtration and then washed on the filter with 21.0 kg of cold (0° C.) water to produce a white solid, weight=41.1 kg (wet). The solid was charged into a 50 gallon reactor equipped with an overhead stirrer, pH probe, thermocouple, condenser, and a heating jacket. Water (102.2 kg) and ethanol (80.2 kg) were added. The mixture was heated to 65°–75° C. The pH of the resulting solution was adjusted to 10.2 using 10N sodium hydroxide (9.1 kg). Heating was discontinued and the mixture was allowed to cool to room temperature. The reaction slurry was cooled to 0° C. and then stirred at this temperature for 1 hour to obtain a thick slurry. The product was collected by filtration and then washed with 55.0 kg of cold (0° C.) water. The product was then dried in vacuo at 50° C. for 24 hours to constant weight to yield 16.1 kg (52.3 M %) of (I); BMS 180048.

EXAMPLE 9

Coupling of compound (IV) with the triethylsilyl compound (III) analog

3-[3-[4-(5-Methoxy-4-pyrimidinyl)-1-piperazinyl] propyl]-N-methyl-2 -(triethylsilyl)-1H-indole-5-methanesulfonamide (II: $R^5$=Et)

Materials:

| | | |
|---|---|---|
| 4-Amino-3-iodo-N-methylbenzenemethane sulfonamide (IV) | 45.1 g | (0.138 mM; from Ex. 1) |
| 1-(5-Methoxy-4-pyridinyl)-1-(4-piperazinyl)-5-triethylsilyl-4-pentyne (III) | 60.0 g | (0.127 mM; from Ex. 6) |
| Sodium carbonate | 48.6 g | (0.459 mM) |
| Triphenylphosphine | 6.60 g | (0.025 mM) |
| Lithium chloride | 7.10 g | (0.167 mM) |
| Palladium acetate | 2.85 g | (0.013 mM) |
| Acetonitrile | 890 mL | |
| Water | 250.0 mL | |
| Trithiocyanuric acid | 6.0 g | (0.034 mM) |
| Decolorizing charcoal | 12.0 g | |

Procedure:

Into a 2-L three-necked round bottom flask equipped with a mechanical stirrer, condenser, nitrogen inlet, temperature probe and a heating mantle were charged the sodium carbonate, triphenylphosphine, lithium chloride, palladium acetate, (IV) and (III), acetonitrile, and water. The reaction slurry was heated to reflux under nitrogen and then stirred at reflux temperature for 4 to 7 hours until the reaction was deemed complete as judged by HPLC. After this period of time, the slurry was allowed to cool to ambient temperature. Trithiocyanuric acid, decolorizing charcoal and acetonitrile (500 mL) were charged into the flask. The resulting triphasic mixture was stirred at ambient temperature for 1 hour and then the slurry was chilled to 0° to 5 ° C. and then stirred at this temperature for 1 hour. The inorganic salts were removed by filtration and then washed with 250 mL of acetonitrile. The filtrate and wash were transferred in a separatory funnel and the aqueous phase was separated from the top organic phase. The organic phase containing the TES-indole intermediate (II) was used "as is" in the next reaction.

EXAMPLE 10

Preparation of BMS 180048 from the triethylsilyl analog of compound (II)

Materials:

| TES-indole derivative (II) | | |
|---|---|---|
| Acetonitrile | 90 mL | |
| THF | 1450 mL | |
| 6N HCl | 127 mL | |
| Sodium chloride | 25 g | (0.428 mM) |
| Ethanol | 110 mL | |
| 1 M $Na_2CO_3$ | 90 mL | |

Procedure:

The solution of compound (II) (Ex. 9) in acetonitrile, and acetonitrile was charged to a 3-L three necked round bottom flask. The reaction solution was cooled to −10° to −15° C. and then treated slowly (over 30 to 90 min) with 6N HCl. The reaction slurry was stirred at ambient temperature for two hours. After this period of time, the reaction may be monitored by HPLC.

The reaction slurry was chilled to 0° C. and then stirred at this temperature for 2 hours to obtain a thick slurry. The product was collect by filtration and then washed with cold THF (250 mL). The product was a light beige to off-white solid. The solid product was transferred in a 1-L flask equipped with a mechanical stirrer, thermocouple, condenser and a heating mantle along with water (600 mL) and decolorizing charcoal (6.0 g). The reaction mixture was heated to 55° to 60° C. and stirred at this temperature for 1 h. After this period of time, the reaction mixture was cooled to 50° to 55° C. and filtered to remove Darco®. The Darco® cake was washed with 55 mL of hot (50° C.) water. Sodium chloride was added to the resulting filtrate and wash. The resulting solution was cooled to ambient temperature over 1 h. The reaction filtrate was cooled to 0° to 5° C. for 2 h to obtain a thick slurry. The HCl salt was collected by filtration and then the cake was washed with 110 mL of cold (0° to 5° C.) ethanol to produce 56.7 g (wet) of a white solid. The solid was charged in a 1-L flask equipped with a mechanical stirrer, condenser, heating mantle, and a thermocouple. Water (190 mL) and ethanol (280 mL) were added. The mixture was heated to 65° to 70° C. The pH of the reaction solution was adjusted to 9.5 to 10.5 by slow addition of 1M sodium carbonate solution (90 mL). Heating was discontinued and the mixture was cooled to room temperature. The reaction slurry was cooled to 0° to 5° C. and then stirred at this temperature for 1 h to obtain a thick slurry. The product was collected by filtration and then washed with 200 mL of cold (0° C.) water. The product was dried in vacuuo at 45° to 50° C. to give 39.8 g of (68.4 M %) of BMS-180048.

It is understood that the reactions described above may be modified by one skilled in organic synthesis in order to produce the products of the reactions in improved yield or to obtain close structural analogs of BMS 180048.

Scheme A
Prior Art Synthesis of BMS 180048 and Analogs
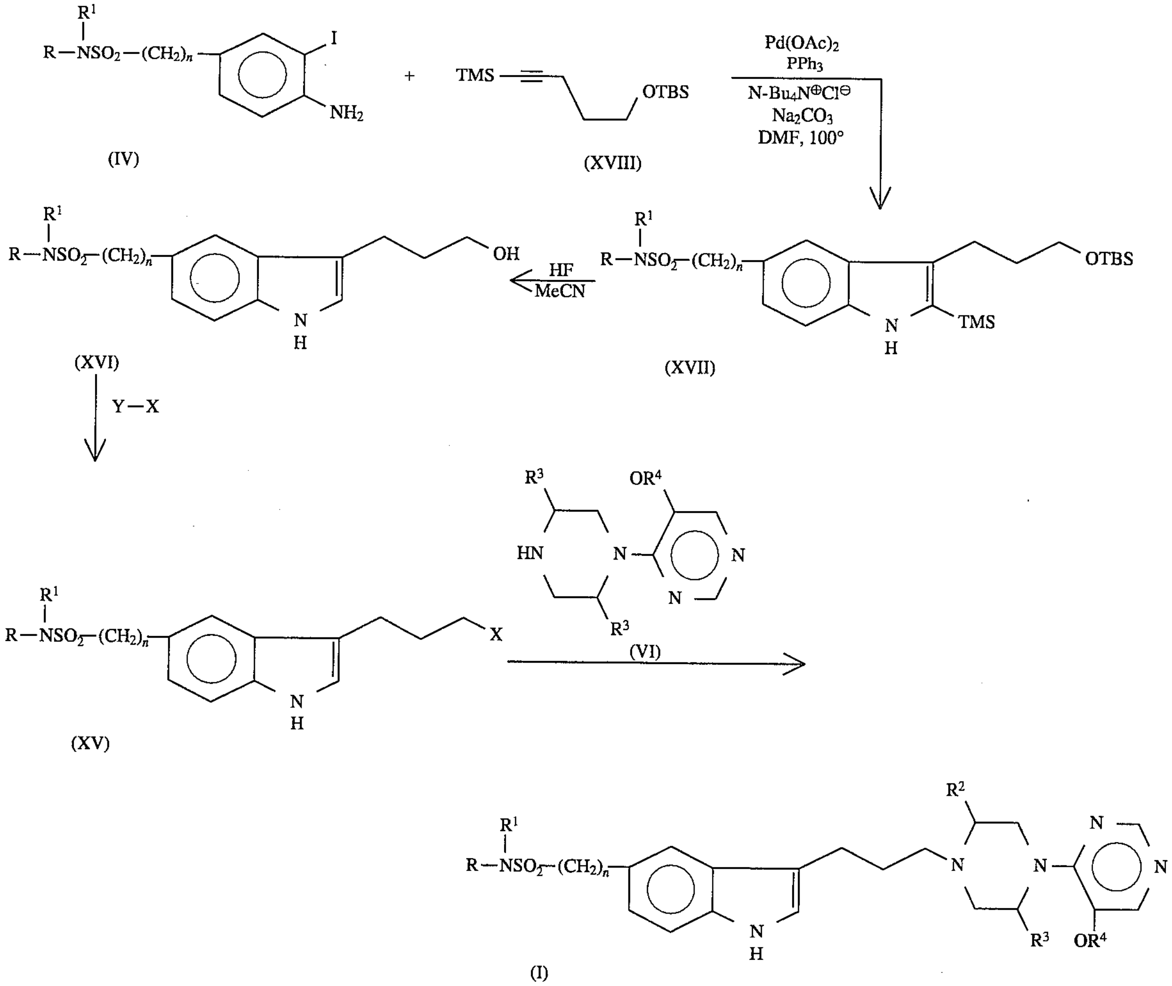
(IV) (XVIII) (XVII) (XVI) (XV) (VI) (I)

Scheme B
Improved Synthesis of BMS 180048 and Analogs
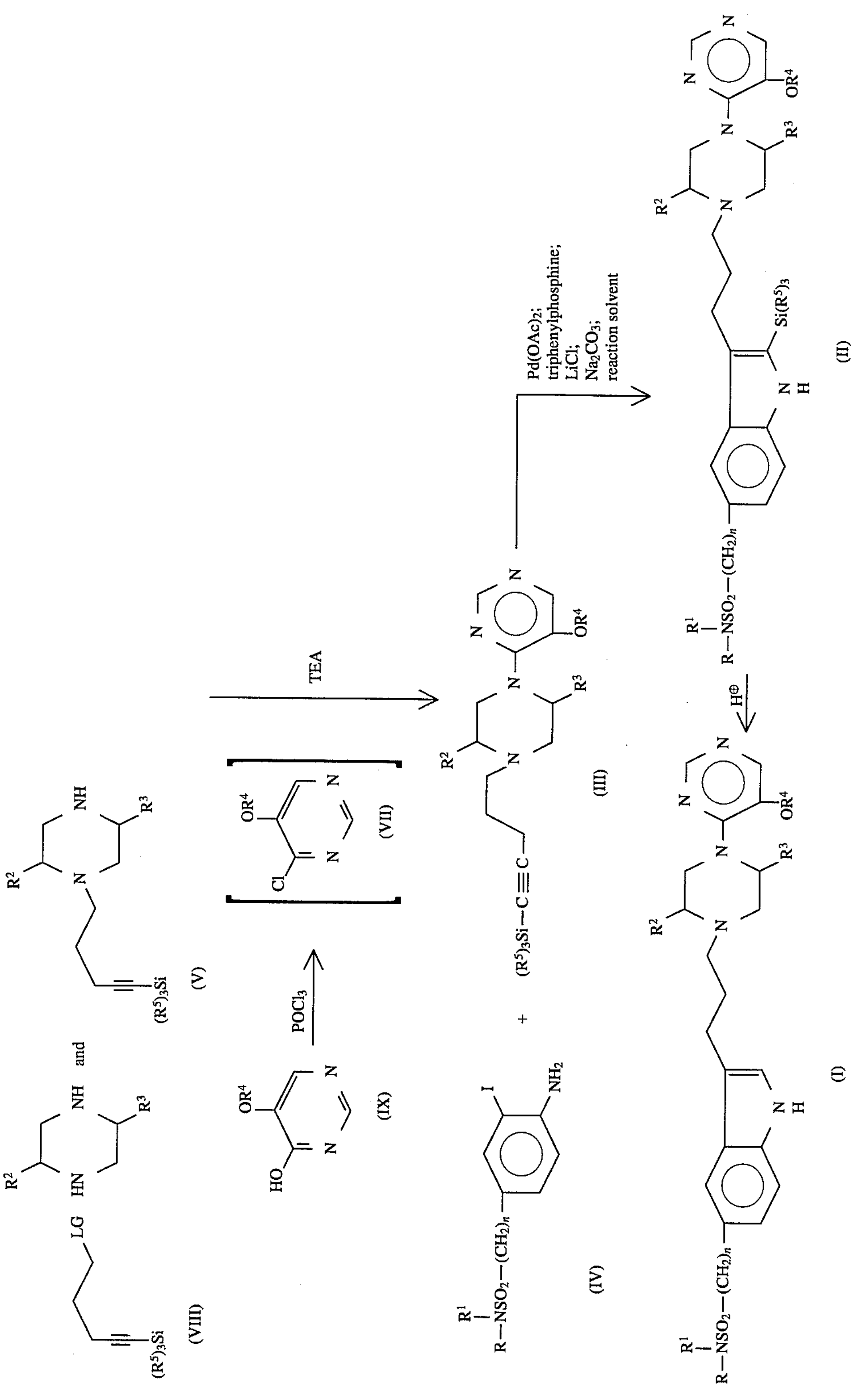
(VIII) and (V)
(IX) (VII)
(IV) + (III)
(II)
(I)

Scheme C

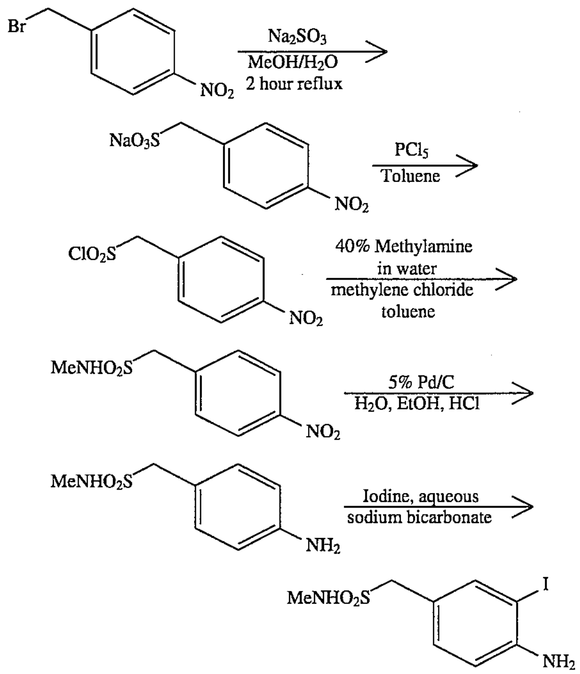

(IV)

We claim:

1. An improved process for preparing certain useful antimigraine agents of Formula (I)

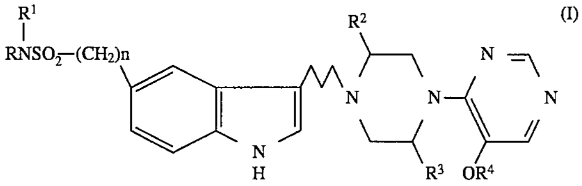

(I)

wherein

R is hydrogen, lower alkyl and trifluoromethyl;

$R^1$ is hydrogen, lower alkyl and lower alkyl-phenyl;

$R^2$ and $R^3$ are independently selected from hydrogen and methyl;

$R^4$ is lower alkyl; and n is zero or the integers 1 and 2;

which comprises a) the reaction of compound (III), wherein $R^5$ is methyl, ethyl or propyl

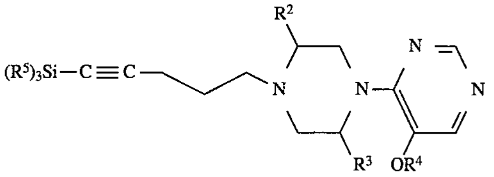

(III)

Scheme D

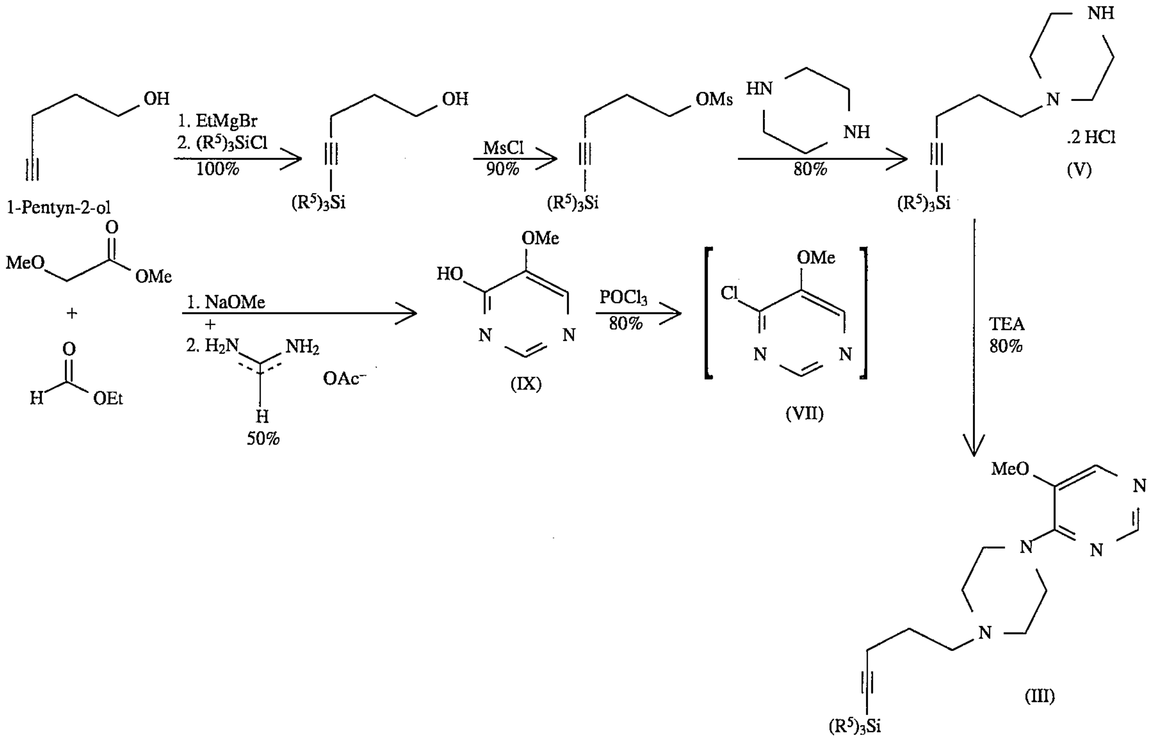

1-Pentyn-2-ol (V)

(IX)

(VII)

(III)

with compound (IV) in

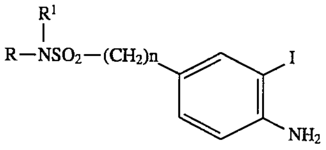

(IV)

a palladium-catalyzed heteroannulation step to give the 2-$(R^5)_3$Si-indole compound (II)

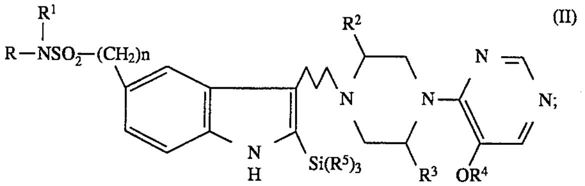

(II)

and b) removal of the trialkylsilyl group of (II) with a mineral acid followed by basification to provide the synthetic product (I)

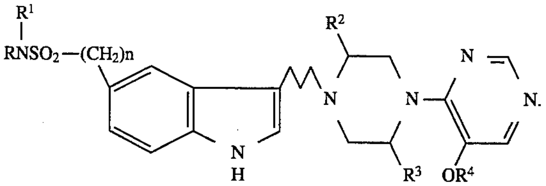

(I)

2. The process of claim 1 wherein R and $R^4$ are methyl; $R^1$, $R^2$ and $R^3$ are hydrogen and n is 1.

3. The process of claim 1 wherein compound (III) is prepared by a) the reaction of compound (VIII), wherein LG is a synthetic organic leaving group,

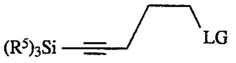

(VIII)

with

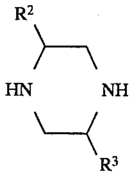

to give compound (V)

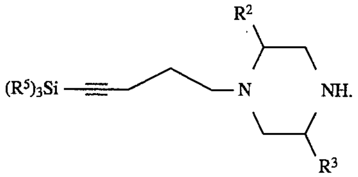

(V)

and b) the reaction of compound (V) with compound (VII)

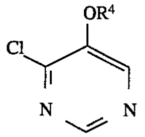

(VII)

to give compound (III).

4. The process of claims 1 or 3 wherein $R^5$ is ethyl.

5. The process of claim 1 wherein the heteroannulation of compounds (III) and (IV) is accomplished with palladium acetate, triphenylphosphine, lithium chloride and sodium carbonate in ethanol.

6. The process of claim 1 wherein the 2-$(R^5)_3$Si-indole intermediate of Formula (II) is converted to the product of Formula (I) by treatment with hydrochloric acid to remove the trialkylsilyl moiety.

7. A compound of Formula (II)

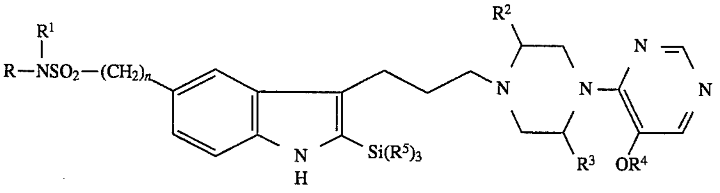

(II)

wherein R is hydrogen, lower alkyl and trifluoromethyl; $R^1$ is hydrogen, lower alkyl and lower alkyl-phenyl; $R^2$ and $R^3$ are independently selected from hydrogen and methyl; $R^4$ is methyl; $R^5$ is methyl or ethyl; and n is zero or the integers 1 and 2.

8. The compound of claim 7 wherein R and $R^4$ are methyl; $R^1$, $R^2$ and $R^3$ are hydrogen; $R^5$ is ethyl and n is 1.

9. A compound of formula (III)

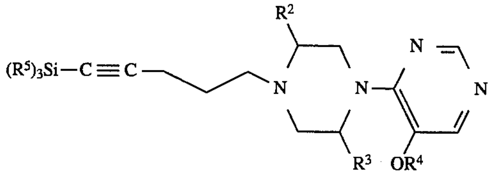

(III)

wherein $R^2$ and $R^3$ are independently selected from hydrogen and methyl; $R^4$ is methyl and $R^5$ is methyl or ethyl.

10. The compound of claim 9 wherein $R^2$ and $R^3$ are hydrogen.

11. The compound of claim 9 wherein $R^5$ is ethyl.

12. An improved process for preparing BMS 180048

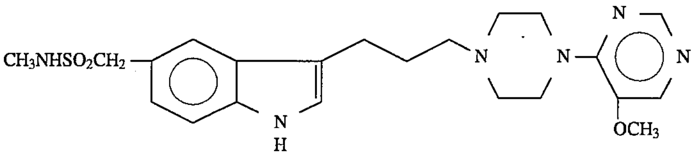

BMS180048 which comprises a) the reaction of compound (V), wherein $R^5$ is methyl or ethyl,

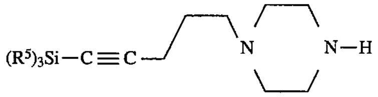

(V)

with compound (VII), wherein $R^4$ is lower alkyl,

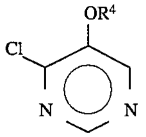

(VII)

to give compound (III)

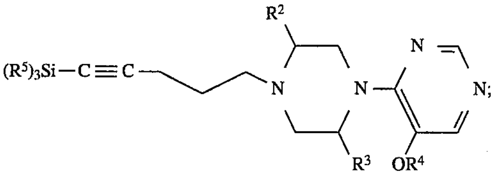

(III)

b) the reaction of compound (III) with compound (IV)

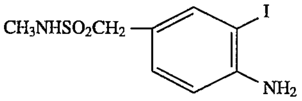

(IV)

in a palladium-catalyzed heteroannulation process to give compound (II)

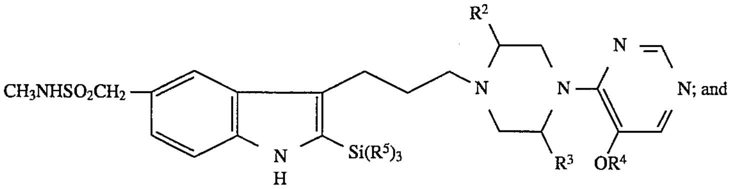

(II)

and c) deprotection of compound (II) with mineral acid to give an acid salt of BMS 180048; and d) recrystallization of the salt from water followed by basification to provide BMS 180048.

13. The process of claim 12 wherein $R^5$ is ethyl.

* * * * *